(12) United States Patent
Umezawa et al.

(10) Patent No.: US 8,105,802 B2
(45) Date of Patent: Jan. 31, 2012

(54) METHOD OF PRODUCING MICROBIAL TRANSGLUTAMINASE

(75) Inventors: Yukiko Umezawa, Kawasaki (JP); Keiichi Yokoyama, Kawasaki (JP); Yoshimi Kikuchi, Kawasaki (JP); Masayo Date, Kawasaki (JP); Norimasa Onishi, Tokyo (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/714,853

(22) Filed: Mar. 1, 2010

(65) Prior Publication Data
US 2010/0159560 A1 Jun. 24, 2010

Related U.S. Application Data

(60) Division of application No. 11/218,780, filed on Sep. 6, 2005, now Pat. No. 7,704,707, which is a continuation of application No. PCT/JP2004/002923, filed on Mar. 5, 2004.

(30) Foreign Application Priority Data

Mar. 7, 2003 (JP) .................. 2003-061623

(51) Int. Cl.
*C12P 21/06* (2006.01)
*C12N 9/10* (2006.01)
*C12N 9/48* (2006.01)

(52) U.S. Cl. .................. 435/68.1; 435/212; 435/193
(58) Field of Classification Search .................. None
See application file for complete search history.

(56) References Cited

U.S. PATENT DOCUMENTS

| 5,156,956 | A | 10/1992 | Motoki et al. |
| 7,252,972 | B2 | 8/2007 | Kikuchi et al. |
| 2003/0082746 | A1 | 5/2003 | Kikuchi et al. |
| 2004/0126847 | A1 | 7/2004 | Kikuchi et al. |
| 2007/0184525 | A1 | 8/2007 | Date et al. |

FOREIGN PATENT DOCUMENTS

| CA | 2518049 | 9/2004 |
| JP | 64-27471 | 1/1989 |
| WO | WO01/23591 | 4/2001 |

OTHER PUBLICATIONS

AAN41655 from Corbett et al., "An extracellular zinc metalloprotease gene of *Burkhodleria cepacia*," Microbiology 2003;149(Pt 8):2263-2271. Alignment with 217-537 of SEQ ID No. 6.
Chang et al., "Extracellular metalloprotease gene of *Streptomyces cacaoi*: structure, nucleotide sequence and characterization of the cloned gene product," Gene 1990;88:87-95.
Chang et al., "Roles of the signal peptide and mature domains in the secretion and maturation of the neutral metalloprotease from *Steptomyces cacaoi*," Biochem J. 1997;321(Pt 1):29-37.
Chang et al., "Extracellular autoprocessing of a metalloprotease from *Streptomyces cacaoi*," J. Biol. Chem. 1992;267(6):3952-3958.
Connell, "Expression systems for use in actinomycetes and related organisms," Curr. Opin. Biotechnol. 2001;12(5):446-449.
Corbett et al., "An extracellular zinc metalloprotease gene of *Burkholderia cepacia*," Microbiology 2003;149(Pt 8):2263-2271.
Database UniProt, Oct. 1, 2000, Bently et al., "Putative neutral zinc metalloprotease," XP002386174, retrieved from EBI, Database accession No. Q9LIF8, 2 pp.
Gayle et al., "Identification of regions in interleukin-1 alpha important for activity," J. Biol. Chem. 1993;268(29):22105-22111.
Kikuchi et al., "Secretion of Active-Form *Streptoverticillium mobaraense* Transglutaminase by *Cornebacterium glutamicum*: Processing of the Pro-Transglutaminase by a Cosecreted Subtilisin-Like Protease from *Streptomyces albogriseolus*," App. Environ. Microbiol. 2003;69(1):358-366.
Kojima et al., "Primary Structure of *Streptomyces griseus* Metalloendopeptidase II," Biosci. Biotechnol. Biochem. 1998;62(7):1392-1398.
Ogawara et al., "beta-lactamase from *Streptomuces cacaoi*. Purification and properties," J. Biol. Chem 1981;256(6):2649-2655.
Olsen et al., "Function-based isolation of novel enzymes from a large library," Nat. Biotechnol. 2000;18(10:1071-1074.
Overall, "Molecular determinants of metalloprotease substrate specificity: matrix metalloprotease substrate binding domains, modules, and exosites," Mol. Biotechnol. 2002;22(1):51-86.
Pasternak et al., "Bacterial pro-transglutaminase from *Streptoverticillium mobaraense* Purification, Characterisation and Sequence of the Zymogen," Eur. J. Biochem. 1998;257:570-576.
Rawlings and Barrett, "Evolutionary families of metalloproteases," Methods Enzymol. 1995;248:183-228.
Tsuyuki et al., "Purification and Characterization of *Streptomyces griseus* Metalloendopeptidases I and II," J. Biochem. 1992;110:339-344.
Whisstock et al., "Prediction of protein function from protein sequence and structure," Q. Rev. Biophys. 2003;36(3):307-340.
International Search Report for PCT App. No. PCT/JP2004/002923 (Jun. 8, 2004).
Supplementary European Search Report for EP Patent App. No. 04717856.1 (Jul. 4, 2006).
First Office Action for Chinese Patent App. No. 200480006224.8 (Dec. 8, 2006).
Office Action from Japanese Patent App. No. 2005-503155 Oct. 13, 2009) with English translation thereof.

*Primary Examiner* — Sheridan Swope
(74) *Attorney, Agent, or Firm* — Shelly Guest Cermak; Cermak Nakajima LLP

(57) ABSTRACT

The present invention provides a neutral metalloprotease from actinomycetes which selectively cleaves a pro-structure part of a microbial protransglutaminase and a gene encoding said neutral metalloprotease. An active microbial transglutaminase having the pro-structure part cleaved can be obtained by culturing a microorganism into which a gene encoding the neutral metalloprotease from actinomycetes according to the present invention has been introduced, whereby producing the neutral metalloprotease from actinomycetes, and reacting it on a microbial protransglutaminase.

3 Claims, 6 Drawing Sheets

(A)

(B)

```
SEQUENCE LISTING

<160> NUMBER OF SEQ ID NOS: 12

<210> SEQ ID NO 1
<211> LENGTH: 20
<212> TYPE: PRT
<213> ORGANISM: Streptoverticillium mobaraense

<400> SEQUENCE: 1

Gly Thr Gly Thr Ser Thr Tyr Ser Gly Thr Val Pro Leu Thr Thr Thr
1               5                   10                  15

Lys Ser Gly Ser
            20

<210> SEQ ID NO 2
<211> LENGTH: 11
<212> TYPE: PRT
<213> ORGANISM: Streptoverticillium mobaraense

<400> SEQUENCE: 2

Gly Thr Gly Asn Ser Gln Gly Ser Gly Gln Val
1               5                   10

<210> SEQ ID NO 3
<211> LENGTH: 30
<212> TYPE: DNA
<213> ORGANISM: Artificial
<220> FEATURE:
```

```
<223> OTHER INFORMATION: PCR primer

<400> SEQUENCE: 3
ggctccggca agagcctcta ctcgggcacg                                         30

<210> SEQ ID NO 4
<211> LENGTH: 30
<212> TYPE: DNA
<213> ORGANISM: Artificial
<220> FEATURE:
<223> OTHER INFORMATION: PCR primer

<400> SEQUENCE: 4
tcagctcacg ttgatcgcgg tccaggaggc                                         30

<210> SEQ ID NO 5
<211> LENGTH: 1614
<212> TYPE: DNA
<213> ORGANISM: Streptoverticillium mobaraense
<220> FEATURE:
<221> NAME/KEY: CDS
<222> LOCATION: (1)..(1611)

<400> SEQUENCE: 5 gtg ttg aga ctc acc gcc acc ccc cgc acc acg gcc ctg cgt gcc gcc       48
Val Leu Arg Leu Thr Ala Thr Pro Arg Thr Thr Ala Leu Arg Ala Ala
1               5                   10                  15 gcc ctc gtc gcc tcc gcg gcc atg gtc gtc gtc ggc gtg cag acg ggc       96
Ala Leu Val Ala Ser Ala Ala Met Val Val Val Gly Val Gln Thr Gly
            20                  25                  30 agc gcg agc gcc tcg ggt gac cgt gac agc gga ggg ctg cca ctg acg      144
Ser Ala Ser Ala Ser Gly Asp Arg Asp Ser Gly Gly Leu Pro Leu Thr
        35                  40                  45 ctc tcc gcg agc cag cgc acc gcc atc cag gag gcc cag agc ggc          192
Leu Ser Ala Ser Gln Arg Thr Ala Ala Ile Gln Glu Ala Gln Ser Gly
    50                  55                  60 gcg tcg gcg acc gcc gcc aag atc ggc ctg agc ggc aag gag aag ctg      240
Ala Ser Ala Thr Ala Ala Lys Ile Gly Leu Ser Gly Lys Glu Lys Leu
65                  70                  75                  80 atc gcc cgc gac gtc gtc aag gac gcc gac ggc acc gtc cac acg cgc      288
Ile Ala Arg Asp Val Val Lys Asp Ala Asp Gly Thr Val His Thr Arg
                85                  90                  95 tac gag cgc acc tac gac ggg ctg ccc gtg ctc ggc ggc gac ctg atc      336
Tyr Glu Arg Thr Tyr Asp Gly Leu Pro Val Leu Gly Gly Asp Leu Ile
            100                 105                 110 gtc cac gag gcg aag gcc gga cgc tcg gtc acc aag gcg aac gac gcg      384
Val His Glu Ala Lys Ala Gly Arg Ser Val Thr Lys Ala Asn Asp Ala
        115                 120                 125 acc ata gcc ctg ccc tcg acc gac gcc tcc ctg gcc ccg gcc gcg gcg      432
Thr Ile Ala Leu Pro Ser Thr Asp Ala Ser Leu Ala Pro Ala Ala Ala
    130                 135                 140 aag aag tcg gcg ctg agc gcc gcc gcc gac cag aag acc gcc aag gcg      480
Lys Lys Ser Ala Leu Ser Ala Ala Ala Asp Gln Lys Thr Ala Lys Ala
145                 150                 155                 160 gac ggc cag gcg ccg cgc aag gtc gtc tgg gcc gcg cag ggc aag ccg      528
Asp Gly Gln Ala Pro Arg Lys Val Val Trp Ala Ala Gln Gly Lys Pro
                165                 170                 175 gtc ctg gcg tac gag acc gtg gtc acg ggc gtg cag aag gac ggc acc      576
Val Leu Ala Tyr Glu Thr Val Val Thr Gly Val Gln Lys Asp Gly Thr
            180                 185                 190 ccg agc gag ctg cac gtg atc acc gac gcg gcg tcc ggc aag aag ctg      624
Pro Ser Glu Leu His Val Ile Thr Asp Ala Ala Ser Gly Lys Lys Leu
        195                 200                 205
```

```
tac cag tac gag gcc atc gag acc ggt acc ggc acc agc acc tac agc      672
Tyr Gln Tyr Glu Ala Ile Glu Thr Gly Thr Gly Thr Ser Thr Tyr Ser
    210             215                 220 ggc acc gtg ccg ctg acc acc acc aag tcg ggc tcc cag tac cag ctc      720
Gly Thr Val Pro Leu Thr Thr Thr Lys Ser Gly Ser Gln Tyr Gln Leu
225             230                 235                 240 aac gac ggc gcg cgc ggc ggc cac aag acg tac gac ctc aac cag ggg      768
Asn Asp Gly Ala Arg Gly Gly His Lys Thr Tyr Asp Leu Asn Gln Gly
                245                 250                 255 acg tcc ggc acc ggt tcg ctg ttc acc aac agc acc gac acc tgg ggc      816
Thr Ser Gly Thr Gly Ser Leu Phe Thr Asn Ser Thr Asp Thr Trp Gly
            260                 265                 270 ggc ggc cgg cag acg gcc ggt gtc gac gcg cac tac ggc gcg gcc gtg      864
Gly Gly Arg Gln Thr Ala Gly Val Asp Ala His Tyr Gly Ala Ala Val
        275                 280                 285 acc tgg gac ttc tac aag aac gtc ttc ggc cgc aac ggc atc cgc aac      912
Thr Trp Asp Phe Tyr Lys Asn Val Phe Gly Arg Asn Gly Ile Arg Asn
    290                 295                 300 gac ggc aag gcc gcc tac tcc cgc gtc cac tac ggc aac agc tac gtg      960
Asp Gly Lys Ala Ala Tyr Ser Arg Val His Tyr Gly Asn Ser Tyr Val
305                 310                 315                 320 aac gcc ttc tgg tcc gac tcc tgc ttc tgc atg acc tac ggc gac ggc     1008
Asn Ala Phe Trp Ser Asp Ser Cys Phe Cys Met Thr Tyr Gly Asp Gly
                325                 330                 335 cag aac aac aag aac ccg ctc acc gcc ctc gac gtg gcg gcc cac gag     1056
Gln Asn Asn Lys Asn Pro Leu Thr Ala Leu Asp Val Ala Ala His Glu
            340                 345                 350 atg agc cac ggc gtc acc gcc gcc acg gcc aag ctc gtg tac agc ggc     1104
Met Ser His Gly Val Thr Ala Ala Thr Ala Lys Leu Val Tyr Ser Gly
        355                 360                 365 gag tcg ggc ggc ctc aac gag gcg acc agc gac atc ttc ggc acc gcc     1152
Glu Ser Gly Gly Leu Asn Glu Ala Thr Ser Asp Ile Phe Gly Thr Ala
    370                 375                 380 gtc gag ttc tac gcc aac aac aag acc gac gtg ggc gac tac ctc atc     1200
Val Glu Phe Tyr Ala Asn Asn Lys Thr Asp Val Gly Asp Tyr Leu Ile
385                 390                 395                 400 ggc gag aag atc aac atc tac ggc gac ggc aag ccg ctg cgc tac atg     1248
Gly Glu Lys Ile Asn Ile Tyr Gly Asp Gly Lys Pro Leu Arg Tyr Met
                405                 410                 415 gac aag ccg agc aag gac ggc aag tcc aag gac agc tgg tac tcc ggc     1296
Asp Lys Pro Ser Lys Asp Gly Lys Ser Lys Asp Ser Trp Tyr Ser Gly
            420                 425                 430 atc ggc ggg gtg gac gtc cac tac tcg tcc ggc ccg gcc aac cac ttc     1344
Ile Gly Gly Val Asp Val His Tyr Ser Ser Gly Pro Ala Asn His Phe
        435                 440                 445 ttc tac ctg ctc tcc gag ggc agc ggg aag aag acg atc aac ggc gtg     1392
Phe Tyr Leu Leu Ser Glu Gly Ser Gly Lys Lys Thr Ile Asn Gly Val
    450                 455                 460 gac tac gac agc ccg acc gcc gac ggg tcc aag gtc acc ggc atc ggc     1440
Asp Tyr Asp Ser Pro Thr Ala Asp Gly Ser Lys Val Thr Gly Ile Gly
465                 470                 475                 480 cgg gac aag gcc cag aag atc tgg tac aag gcg ctg acc acg cag ttc     1488
Arg Asp Lys Ala Gln Lys Ile Trp Tyr Lys Ala Leu Thr Thr Gln Phe
                485                 490                 495 acc tcg aac acc aac tac gcc aag gcg cgc acc ggc acc ctg aac gcc     1536
Thr Ser Asn Thr Asn Tyr Ala Lys Ala Arg Thr Gly Thr Leu Asn Ala
            500                 505                 510 gcc gcg tcg ctc tac ggc aac aac agc gcg gag tac aag gcg gtg gcg     1584
Ala Ala Ser Leu Tyr Gly Asn Asn Ser Ala Glu Tyr Lys Ala Val Ala
        515                 520                 525
```

```
                                        -continued gcg gcc tgg tcc gcc atc aac gtc aag tag                       1614
Ala Ala Trp Ser Ala Ile Asn Val Lys
        530                 535

<210> SEQ ID NO 6
<211> LENGTH: 537
<212> TYPE: PRT
<213> ORGANISM: Streptoverticillium mobaraense

<400> SEQUENCE: 6

Val Leu Arg Leu Thr Ala Thr Pro Arg Thr Ala Leu Arg Ala Ala
1               5                   10                  15

Ala Leu Val Ala Ser Ala Ala Met Val Val Gly Val Gln Thr Gly
                20                  25                  30

Ser Ala Ser Ala Ser Gly Asp Arg Asp Ser Gly Gly Leu Pro Leu Thr
            35                  40                  45

Leu Ser Ala Ser Gln Arg Thr Ala Ala Ile Gln Glu Ala Gln Ser Gly
    50                  55                  60

Ala Ser Ala Thr Ala Ala Lys Ile Gly Leu Ser Gly Lys Glu Lys Leu
65                  70                  75                  80

Ile Ala Arg Asp Val Val Lys Asp Ala Asp Gly Thr Val His Thr Arg
                85                  90                  95

Tyr Glu Arg Thr Tyr Asp Gly Leu Pro Val Leu Gly Gly Asp Leu Ile
                100                 105                 110

Val His Glu Ala Lys Ala Gly Arg Ser Val Thr Lys Ala Asn Asp Ala
            115                 120                 125

Thr Ile Ala Leu Pro Ser Thr Asp Ala Ser Leu Ala Pro Ala Ala Ala
        130                 135                 140

Lys Lys Ser Ala Leu Ser Ala Ala Asp Gln Lys Thr Ala Lys Ala
145                 150                 155                 160

Asp Gly Gln Ala Pro Arg Lys Val Val Trp Ala Ala Gln Gly Lys Pro
                165                 170                 175

Val Leu Ala Tyr Glu Thr Val Val Thr Gly Val Gln Lys Asp Gly Thr
            180                 185                 190

Pro Ser Glu Leu His Val Ile Thr Asp Ala Ala Ser Gly Lys Lys Leu
        195                 200                 205

Tyr Gln Tyr Glu Ala Ile Glu Thr Gly Thr Gly Thr Ser Thr Tyr Ser
    210                 215                 220

Gly Thr Val Pro Leu Thr Thr Thr Lys Ser Gly Ser Gln Tyr Gln Leu
225                 230                 235                 240

Asn Asp Gly Ala Arg Gly His Lys Thr Tyr Asp Leu Asn Gln Gly
                245                 250                 255

Thr Ser Gly Thr Gly Ser Leu Phe Thr Asn Ser Thr Asp Thr Trp Gly
                260                 265                 270

Gly Gly Arg Gln Thr Ala Gly Val Asp Ala His Tyr Gly Ala Ala Val
            275                 280                 285

Thr Trp Asp Phe Tyr Lys Asn Val Phe Gly Arg Asn Gly Ile Arg Asn
        290                 295                 300

Asp Gly Lys Ala Ala Tyr Ser Arg Val His Tyr Gly Asn Ser Tyr Val
305                 310                 315                 320

Asn Ala Phe Trp Ser Asp Ser Cys Phe Cys Met Thr Tyr Gly Asp Gly
                325                 330                 335

Gln Asn Asn Lys Asn Pro Leu Thr Ala Leu Asp Val Ala Ala His Glu
            340                 345                 350

Met Ser His Gly Val Thr Ala Ala Thr Ala Lys Leu Val Tyr Ser Gly
```

Glu Ser Gly Gly Leu Asn Glu Ala Thr Ser Asp Ile Phe Gly Thr Ala
            370                 375                 380

Val Glu Phe Tyr Ala Asn Asn Lys Thr Asp Val Gly Asp Tyr Leu Ile
385                 390                 395                 400

Gly Glu Lys Ile Asn Ile Tyr Gly Asp Gly Lys Pro Leu Arg Tyr Met
                405                 410                 415

Asp Lys Pro Ser Lys Asp Gly Lys Ser Lys Asp Ser Trp Tyr Ser Gly
            420                 425                 430

Ile Gly Gly Val Asp Val His Tyr Ser Ser Gly Pro Ala Asn His Phe
                435                 440                 445

Phe Tyr Leu Leu Ser Glu Gly Ser Gly Lys Lys Thr Ile Asn Gly Val
            450                 455                 460

Asp Tyr Asp Ser Pro Thr Ala Asp Gly Ser Lys Val Thr Gly Ile Gly
465                 470                 475                 480

Arg Asp Lys Ala Gln Lys Ile Trp Tyr Lys Ala Leu Thr Thr Gln Phe
                485                 490                 495

Thr Ser Asn Thr Asn Tyr Ala Lys Ala Arg Thr Gly Thr Leu Asn Ala
            500                 505                 510

Ala Ala Ser Leu Tyr Gly Asn Asn Ser Ala Glu Tyr Lys Ala Val Ala
            515                 520                 525

Ala Ala Trp Ser Ala Ile Asn Val Lys
            530                 535

<210> SEQ ID NO 7
<211> LENGTH: 25
<212> TYPE: DNA
<213> ORGANISM: Artificial
<220> FEATURE:
<223> OTHER INFORMATION: PCR primer

<400> SEQUENCE: 7
tcgggtgacc gtgacagcgg agggc                                    25

<210> SEQ ID NO 8
<211> LENGTH: 25
<212> TYPE: DNA
<213> ORGANISM: Artificial
<220> FEATURE:
<223> OTHER INFORMATION: PCR primer

<400> SEQUENCE: 8
gcgagtagcc gaggtcgatc acgtc                                    25

<210> SEQ ID NO 9
<211> LENGTH: 26
<212> TYPE: DNA
<213> ORGANISM: Artificial
<220> FEATURE:
<223> OTHER INFORMATION: PCR primer

<400> SEQUENCE: 9
aaattcctgt gaattagctg atttag                                   26

<210> SEQ ID NO 10
<211> LENGTH: 44
<212> TYPE: DNA
<213> ORGANISM: Artificial
<220> FEATURE:
<223> OTHER INFORMATION: PCR primer

<400> SEQUENCE: 10

```
ctccgctgtc acggtcaccc gatgccgttg ccacaggtgc ggcc                    44

<210> SEQ ID NO 11
<211> LENGTH: 9
<212> TYPE: PRT
<213> ORGANISM: Streptoverticillium mobaraense

<400> SEQUENCE: 11

Gly Pro Ser Phe Arg Ala Pro Asp Ser
1               5

<210> SEQ ID NO 12
<211> LENGTH: 6
<212> TYPE: PRT
<213> ORGANISM: Streptoverticillium mobaraense

<400> SEQUENCE: 12

Phe Arg Ala Pro Asp Ser
1               5
```

METHOD OF PRODUCING MICROBIAL TRANSGLUTAMINASE

This application is a divisional under 35 U.S.C. §120 of U.S. patent application Ser. No. 11/218,780, filed on Sep. 6, 2005, now U.S. Pat. No. 7,704,707, which is a continuation under 35 U.S.C. §120 of PCT/JP2004/002923, filed Mar. 5, 2004, which claimed priority to Japanese Patent App. No. 2003-061623, filed on Mar. 7, 2003, the entireties of which are incorporated by reference. The Sequence Listing in electronic format filed herewith is also hereby incorporated by reference in its entirety (File Name: 20100301T_US-183D_Seq_List; File Size: 158 KB; Date Created: Mar. 1, 2010).

BACKGROUND OF THE INVENTION

1. Field of the Invention

The present invention relates to a protease which efficiently cleaves the pro-structure part of pro-transglutaminase resulting in an active transglutaminase, and to a nucleic acid encoding the protease, wherein the pro-transglutaminase is produced by actinomycetes. The present invention also relates to a method of producing microbial transglutaminase in its active form using the protease. Additionally, the present invention relates to a method of producing a neutral metalloprotease.

2. Brief Description of the Related Art

Transglutaminase is an enzyme which catalyzes the acyl-transfer reaction of γ-carboxylamide groups in the peptide chain of the protein. When the enzyme reacts with a protein, the formation of the cross-linkage ε-(γ-Glu)-Lys, and the replacement of Gln with Glu by deamidation can occur. Transglutaminases have been used to manufacture gelled food products such as jelly, yogurt, cheese, or gelled cosmetics and others, and to improve the quality of meat, etc. (Japanese publication of examined application (JP-Kokoku) No. 1-50382). Moreover, transglutaminase is highly useful in industry in that it has been used to manufacture materials for thermostable microcapsules, carriers for immobilized enzyme, etc.

Expression of animal transglutaminase activity is calcium-dependent, and transglutaminases from microorganisms (microbial transglutaminase(s), which is/are also referred to as "MTG(s)" hereinafter), have been previously reported to also be calcium-independent. A microbial transglutaminase from a bacterium belonging to genus Streptoverticillium has been reported. Such Streptoverticillium bacteria include, for example, Streptoverticillium griseocarneum IFO 12776, Streptoverticillium cinnamoneum sub sp. cinnamoneum IFO 12852, Streptoverticillium mobaraense (hereinafter, S. mobaraense) IFO 13819, and others (Publication of unexamined Japanese patent application (JP-Kokai) No. 64-27471).

Because these transglutaminases, however, have been produced via purification from cultures of the microorganisms described above, problems have been reported regarding the produced amount, production efficiency, and the like. Then, in an attempt to more efficiently secrete heterologous proteins, a method was reported using a coryneform bacterium as a host, and a fused protein whereby transglutaminase was connected downstream of the signal peptide domain of the coryneform bacterium, and the transglutaminase was efficiently secreted resulting in a high yield of transglutaminase (WO 01/23591). In this study, a method is also described wherein inactive MTG is secreted as pro-transglutaminase (referred to as "pro-MTG" hereinafter) whereby a pro-structure part is connected to MTG, and then this pro-structure part is cleaved by a protease to convert it into an active transglutaminase. A further method is described wherein an active transglutaminase is directly produced in a culture medium by co-expressing SAM-P45, which is a serine protease derived from actinomycetes, in a sufficient amount in a coryneform bacterium which also produces the pro-MTG.

Although a method in which an active transglutaminase is directly produced by co-expressing pro-MTG and a protease which allows cleavage of the pro-structure part of the pro-MTG in a coryneform bacterium is assumed to be an extremely efficient method of producing transglutaminase, the substrate specificity of SAM-P45 is not very strict, and it may digest and degrade not only the pro-structure part of the pro-MTG but also the transglutaminase itself to some degree. Therefore, the handling of SAM-P45 may not be easy. When SAM-P45 is used, therefore, the production method of transglutaminase should be strictly controlled such that degradation of the transglutaminase in the culture medium will not occur.

There is still, therefore, demand for a protease which can selectively cleave only the pro-structure part of pro-MTG, with as little degradation of the transglutaminase itself as possible during the production of an active transglutaminase.

A dispase derived from Bacillus polymyxa is known (Eur. J. Biochem., vol. 257, p. 570-576 (1998)) to be an enzyme besides SAM-P45 which cleaves the pro-structure part of pro-MTG. A large amount of the enzyme, however, is required to cleave the pro-structure part, and there is a risk of degrading the transglutaminase itself. In addition, dispase is a reagent in cell culture, so it is expensive when used an enzyme for industrial use.

SUMMARY OF THE INVENTION

There remains a need for a protease which can selectively cleave solely the pro-structure part of pro-MTG, and degrade the transglutaminase itself as little as possible during the production of an active transglutaminase, as mentioned above. Additionally, if proteases which selectively cleave only the pro-structure part of pro-MTG could be used, and thereby cause as little degradation as possible of the transglutaminase itself, it would be advantageous for the production of an active transglutaminase. Furthermore, if proteases for production of transglutaminase which selectively cleave the pro-structure part of pro-MTG were able to be secreted extracellularly, it would be more preferable because active transglutaminases could be directly produced in the culture medium by co-expressing them with the pro-MTG.

It is an object of the present invention to provide a method of producing an active transglutaminase from a microbial protransglutaminase comprising contacting a neutral metalloprotease with the protransglutaminase, wherein said neutral metalloprotease is produced by culturing a microorganism into which a gene encoding the neutral metalloprotease from actinomycetes has been introduced, and recovering an active microbial transglutaminase.

It is a further object of the present invention to provide the method as described above, wherein said microorganism comprises a coryneform bacterium.

It is a further object of the present invention to provide the method as described above, wherein said neutral metalloprotease from actinomycetes comprises characteristics selected from the group consisting of a molecular weight of about 35,000, an optimum pH of pH7.0, stability at pH of pH4-10, an optimum temperature of about 45° C., stability below about 50° C., and said metalloprotease is strongly inhibited by ethylene diamine tetraacetic acid, 1,10-phenanthroline, phosphoramidon, and *Streptomyces* subtilisin inhibitor (SSI) from actinomycetes.

It is a further object of the present invention to provide the method as described above, wherein said neutral metalloprotease from actinomycetes comprises characteristics selected from the group consisting of a molecular weight of about 71,000, an optimum pH of 7.0, stability at pH of 5-10, an optimum temperature of about 55° C., and said metalloprotease is strongly inhibited by ethylene diamine tetraacetic acid, 1,10-phenanthroline, phosphoramidon, dithiothreitol, and *Streptomyces* subtilisin inhibitor (SSI) derived from actinomycetes.

It is a further object of the present invention to provide a neutral metalloprotease from actinomycetes comprising characteristics selected from the group consisting of a molecular weight of about 35,000, an optimum pH of pH7.0, stability at pH of pH4-10, an optimum temperature of about 45° C., stability below about 50° C., and said metalloprotease is strongly inhibited by ethylene diamine tetraacetic acid, 1,10-phenanthroline, phosphoramidon, and *Streptomyces* subtilisin inhibitor (SSI) from actinomycetes.

It is a further object of the present invention to provide a neutral metalloprotease from actinomycetes comprising characteristics selected from the group consisting of a molecular weight of about 71,000, an optimum pH of 7.0, stability at pH of 5-10, an optimum temperature of about 55° C., and said metalloprotease is strongly inhibited by ethylene diamine tetraacetic acid, 1,10-phenanthroline, phosphoramidon, dithiothreitol, and *Streptomyces* subtilisin inhibitor (SSI) derived from actinomycetes.

It is a further object of the present invention to provide a nucleic acid molecule encoding said protease described above.

It is a further object of the present invention to provide a method of producing said protease comprising culturing a coryneform bacterium into which the nucleic acid molecule as described above has been introduced, and recovering said neutral metalloprotease which has been secreted extracellularly.

DESCRIPTION OF THE PREFERRED EMBODIMENTS

Figure 1:
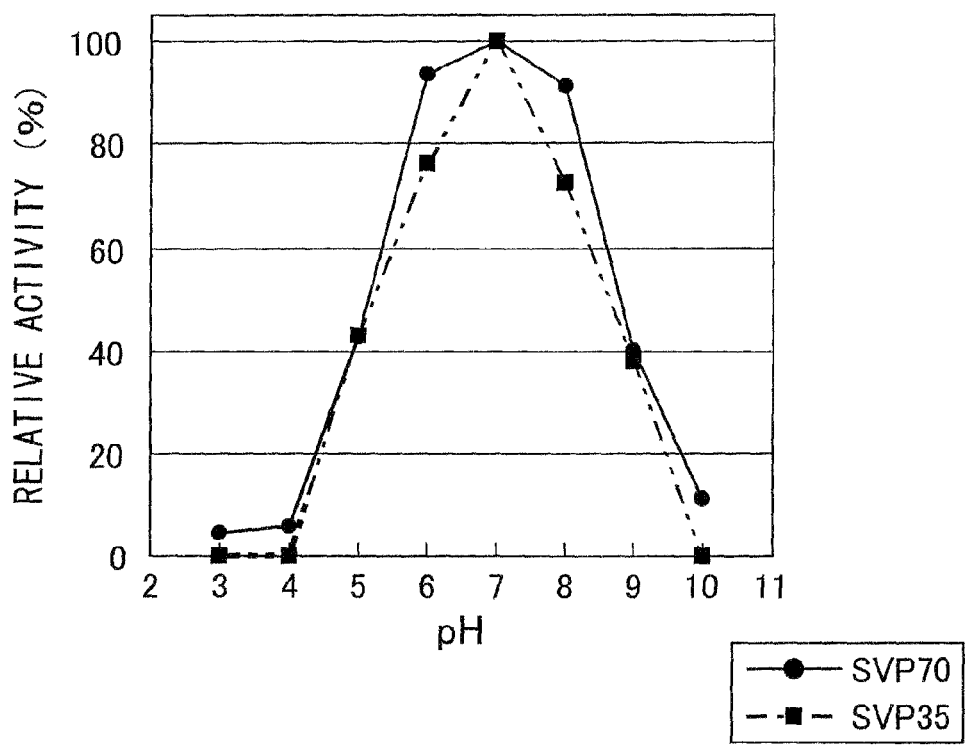
FIG. 1 is a graph which shows the pH dependence of SVP35 and SVP70 activity.

The present invention describes a protease which selectively cleaves the pro-structure part of pro-MTG, but degrades the transglutaminase itself as little as possible, and the isolation and purification of a neutral metalloprotease having such a property. The present invention also describes a DNA encoding said protease, its introduction into a host coryneform bacterium, and the successful secretory expression. In addition, the described enzyme was actually reacted with the pro-MTG to cleave the pro-structure part, and the active transglutaminase was recovered. The present invention describes the identification of neutral metalloproteases derived from microorganisms from other sources which have an equivalent function, and which have been proven similarly useful for the production of an active MTG.

Namely, the present invention is a neutral metalloprotease from actinomycetes which has high selectivity in cleaving the pro-structure part of pro-MTG, and a nucleic acid molecule encoding it.

The present invention also encompasses a method of producing an active MTG by cleaving a pro-structure part of a pro-MTG with a neutral metalloprotease.

The present invention also encompasses a method of producing said metalloprotease by introducing a nucleic acid molecule which encodes said neutral metalloprotease into a coryneform bacterium, culturing this coryneform bacterium, thereby allowing the expression of said neutral metalloprotease, and recovering the extracellularly secreted metalloprotease.

More specifically, the present invention encompasses a neutral metalloprotease SVP35 from actinomycetes having the following properties:
1) Molecular weight: about 35,000 (as measured by SDS-PAGE)
2) Optimum pH: 6.0-8.0, more specifically 6.5-7.5, in particular around 7.0
3) pH Stability: pH of 4-10
4) Optimum temperature: about 45° C.
5) Temperature stability: it is stable below about 50° C.
6) It is strongly inhibited by ethylene diamine tetraacetic acid, 1,10-phenanthroline, and phosphoramidon which are metalloprotease inhibitors, and by *Streptomyces* subtilisin inhibitor (SSI) from actinomycetes.

The present invention also encompasses a neutral metalloprotease SVP70 having the following properties:
1) Molecular weight: about 71,000 (as measured by SDS-PAGE)
2) Optimum pH: the range of 6.0-8.0, more specifically 6.5-7.5, in particular around 7.0
3) pH Stability: pH of 5-10
4) Optimum temperature: the range of about 50° C.-55° C., in particular around 55° C.
5) It undergoes a strong inhibitory action by ethylene diamine tetraacetic acid, 1,10-phenanthroline, and phosphoramidon which are metalloprotease inhibitors, dithiothreitol which is a SH-reductant, and by *Streptomyces* subtilisin inhibitor (SSI) derived from actinomycetes.

The present invention also encompasses a nucleic acid molecule encoding said SVP35 or SVP70.

The present invention also encompasses a method of producing an active MTG, comprising cleaving the pro-structure part of pro-MTG by said SVP35 or SVP70.

Furthermore, the present invention is a method of producing SVP35 or SVP70, comprising introducing a nucleic acid molecule encoding said SVP35 or SVP70 into a coryneform bacterium, culturing the coryneform bacterium into which said nucleic acid molecule has been introduced, and recovering the extracellularly secreted SVP35 or SVP70.

In general, it is known that a secretory protein is translated as a prepeptide or a prepropeptide and thereafter its signal peptide (the pre-part) is cleaved resulting in a mature peptide or propeptide. The propeptide is then cleaved at the domain referred to as a pro-structure, resulting in a mature peptide. As used herein, the pro-structure part of a secretory protein may be simply referred to as "pro-structure". In addition, as used herein, "a signal sequence" refers to the sequence which is located at the N-terminus of a secretory protein precursor and which is not present in a naturally occurring mature protein. The phrase "a signal peptide" refers to the peptide which is cleaved from the protein precursor. Generally, a signal sequence is cleaved by a protease following extracellular secretion.

As used herein, a protein which does not contain a signal peptide but does contain a pro-structure part may be referred to as a "proprotein", for example "protransglutaminase" or "pro-MTG". As used herein, the pro-structure part of a secretory protein may be simply referred to as "a pro-structure" or "a pro-structure part", and these terms can herein be used interchangeably.

Among proteases which are assumed to be easily expressed in a coryneform bacterium, a protease having high specificity and selectivity for the substrate of interest was sought, i.e. a protease which selectively cleaves the pro-structure part of a pro-MTG, with as little degradation as possible of the transglutaminase itself.

When MTG is secreted extracellularly by an actinomycetes, it had been assumed to be secreted first as a pro-MTG, followed by the cleavage of the pro-structure part pro-MTG, resulting in an active MTG (Eur. J. Biochem., vol. 257, p. 570-576 (1998)). Accordingly, a protease that cleaves the pro-structure part of a pro-MTG within MTG-producing actinomycetes was expected to be present. Since this protease is originally a protease that cleaves the pro-structure part, it is expected that the protease has a high selectivity for substrates and cleaves only the pro-structure part, while acting on the MTG itself to a lesser degree.

In addition, both a structural gene of a pro-MTG of actinomycetes and a structural gene of the protease SAM-P45 can be effectively expressed in a coryneform bacterium, and secreted extracellularly. Based on this information, an investigation was conducted in order to find the protease of interest from a MTG-producing bacterium which is an actinomycetes, and as a result, it was revealed that the MTG-producing strain *Streptoverticillium mobaraense* had high cleavage selectivity for the pro-structure part of the pro-MTG and produces new neutral metalloproteases useful for the production of an active MTG. These neutral metalloproteases were isolated and purified, and their enzymological properties were demonstrated. Furthermore, the amino acid sequences of the N-terminal parts of these metalloproteases were determined, and the genes encoding the metalloproteases were obtained.

In addition, the enzyme gene was introduced into a coryneform bacterium, allowing the expression of it in a system using a coryneform bacterium as a host, and as a result, the enzyme was secreted extracellularly. Furthermore, the enzyme was practically contacted with a pro-MTG of a pro-structure part, resulting in the cleavage of the pro-structure part to yield an active transglutaminase. Neutral metalloproteases from microorganisms from other sources having an equivalent function were also found, and which have been found to be similarly useful for the production of an active MTG.

More specific embodiments of the present invention will be illustrated hereinafter.

The neutral metalloproteases according to the present invention can be prepared from the surfaces of a cultured actinomycetes or culture supernatant of the actinomycetes, including *Streptoverticillium mobaraense, Streptomyces griseus, Streptomyces coelicolor*, etc.

Next, the newly found neutral metalloproteases of *Streptoverticillium mobaraense* IFO13819 are described.

The cultivation of a bacterium to obtain the neutral metalloprotease according to the present invention, for example, an actinomycetes as described above, can be carried out according to the methods conventionally used for the cultivation of actinomycetes. Namely, a common medium containing conventional carbon sources, nitrogen sources, inorganic ions, and others can be used as a medium for the culture. Glucose, starch, sucrose, and others can be used as the carbon sources. Peptone, yeast extract, meat extract, malt extract, ammonium salt, and others are optionally used as the nitrogen sources, if necessary. The culture may be conducted under aerobic conditions which are appropriately controlled within the pH range of between pH 5.0 and 8.5 and the temperature range between 15° C. and 37° C. For the production of the neutral metalloproteases according to the present invention, the culture is preferably continued so that the maximum amount of the desired neutral metalloprotease may be achieved, and then it can be terminated. Although the suitable culture period depends on the temperature, pH, and the type of medium, usually the period is preferably about 1 to 12 days. After the culturing period, the culture may be separated into the cells and the culture supernatant by centrifugation and the like.

The new neutral metalloproteases according to the present invention can be obtained from the culture supernatant and/or the recovered cells, in particular, from the surface of the cells. To purify the enzyme, methods which are conventionally used for purifying an enzyme, for example, an ammonium sulfate salting-out technique, gel filtration technique, ion-exchange chromatography, hydrophobic chromatography, and the like can be adopted. The protease can be purified more efficiently using high performance liquid chromatography (HPLC) etc. The enzyme activity of the neutral metalloprotease obtained in this way can be determined by reacting the enzyme with a peptide which contains a region connecting the pro-part of a protransglutaminase and a mature transglutaminase, for example, a synthetic peptide Gly-Pro-Ser-Phe-Arg-Ala-Pro-Asp-Ser (SEQ ID NO: 11) (Peptide Institute) as a substrate and the reduced amount of the substrate can be calculated.

As mentioned above, the neutral metalloprotease according to the invention purified from the recovered cells, in particular from the surface of the cells, or from the supernatant of the culture, can be analyzed for the N-terminal amino acid sequence by a gas phase protein sequencer to determine the partial amino acid sequence. Furthermore, the enzymatic properties (optimum pH, pH stability, optimum temperature, the effect of an inhibitor, etc.) of the isolated and purified neutral metalloprotease can be examined.

In one embodiment of the present invention, the neutral metalloprotease SVP35 was obtained from the surface of the cells of *Streptoverticillium mobaraense* and the neutral metalloprotease SVP70 can be obtained from the culture supernatant of *Streptoverticillium mobaraense*.

In one embodiment of the present invention, the neutral metalloprotease according to the invention is the neutral metalloprotease SVP35 having the following properties:
1) Molecular weight: about 35,000 (as measured by SDS-PAGE)
2) Optimum pH: 6.0-8.0, more specifically 6.5-7.5, in particular around 7.0
3) pH Stability: pH of 4-10
4) Optimum temperature: about 45° C.
5) Temperature stability: it is stable below about 50° C.
6) Inhibitors: it is strongly inhibited by ethylene diamine tetraacetic acid, 1,10-phenanthroline and phosphoramidon which are metalloprotease inhibitors, and by *Streptomyces* subtilisin inhibitor (SSI) derived from actinomycetes.

In another embodiment of the present invention, the neutral metalloprotease according to the present invention is the neutral metalloprotease SVP70 having the following properties:
1) Molecular weight: about 71,000 (as measured by SDS-PAGE)
2) Optimum pH: 6.0-8.0, more specifically 6.5-7.5, in particular around 7.0
3) pH Stability: pH of 5-10
4) Optimum temperature: about 50° C.-55° C., in particular around 55° C.
5) Inhibitors: it is strongly inhibited by ethylene diamine tetraacetic acid, 1,10-phenanthroline and phosphoramidon which are metalloprotease inhibitors, dithiothreitol which is a SH-reductant, and by *Streptomyces* subtilisin inhibitor (SSI) from actinomycetes.

When SVP35 or SVP70 is contacted with pro-MTG, both of them show highly selective cleavage activity on the pro-structure part of the MTG. Namely, since both of the enzymes are characterized by converting the pro-MTG into the active MTG efficiently, while the activity for degrading the resulting active MTG itself is low, both of them are suitable enzymes for producing an active MTG using pro-MTG as a raw material. The N-terminal amino acid sequences of the two new neutral metalloproteases are shown in SEQ ID NO: 1 for SVP35, and in SEQ ID NO: 2 for SVP70, which reveals the homology between these sequences. Therefore, sequences having any homology with these proteases in their N-terminal amino acid sequences were searched and a metalloprotease SGMP II (J. Biochem. Vol. 110, p. 339-344 (1991)) from *Streptomyces griseus* as well as the three metalloproteases (GenBank/EMBL/DDBJ CAB76000, CAB76001, CAB69762) from *Streptomyces coelicolor*, and the like were found. These proteases can also be used in the same manner as SVP35 and SVP70 for selective cleavage of the pro-structure part of a pro-MTG, and they can be used to produce an active MTG using a pro-MTG as the raw material.

Next, a method of producing the neutral metalloprotease according to the present invention by recombinant DNA technique will be described.

A number of examples of producing useful proteins including enzymes, physiologically active substances, and the like using recombinant DNA techniques have been known. The advantage of using recombinant DNA techniques is the ability to mass-produce useful proteins that exist in small quantities in nature.

To produce the neutral metalloprotease according to the present invention by using recombinant DNA techniques, a genetic construct is generated first which contains a promoter, a sequence encoding a proper signal peptide, a nucleic acid fragment encoding the neutral metalloprotease according to the invention, and a regulatory sequence (an operator or terminator, etc.) which is necessary to express the gene for the neutral metalloprotease in a coryneform bacterium, and properly positioned so that they can function. The neutral metalloprotease according to the invention may have a pro-structure part at the N-terminal. Vectors, which can be used for this construct, are not particularly limited and include any one which can function in a coryneform bacterium, and may be those which autonomously replicate such as plasmids or which are integrated into the chromosome of the bacterium. When a coryneform bacterium is used as a host, plasmids derived from coryneform bacteria are particularly preferable as vectors. These include, for example, pHM1519 (Agric. Biol. Chem., 48, 2901-2903 (1984)), pAM330 (Agric. Biol. Chem., 48, 2901-2903 (1984)), and modified plasmids, which possess drug-resistant genes.

Examples of *Corynebacterium* which can be used as a host bacterium in the present invention include mutant strains derived from wild-type strains including *Brevibacterium saccharolyticum* ATCC14066, *Brevibacterium immariophilum* ATCC14068, *Brevibacterium lactofermentum* (*Corynebacterium glutamicum*) ATCC13869, *Brevibacterium roseum* ATCC13825, *Brevibacterium flavum* (*Corynebacterium glutamicum*) ATCC14067, *Corynebacterium acetoacidophilum* ATCC13870, *Corynebacterium glutamicum* ATCC13032, *Corynebacterium lilium* (*Corynebacterium glutamicum*) ATCC15990, *Brevibacterium ammoniagenes* (*Corynebacterium ammoniagenes*) ATCC6871 and the like, or mutant strains derived from mutants strain of these wild-types.

Mutant strains which can be used in the present invention include, for example, mutant strains defective in the ability to produce glutamate, mutant strains for amino acid production, such as lysine and the like, and mutant strains modified to produce other substances such as nucleic acids, for example, inosine. Such mutant strains can be obtained by treatment with ultraviolet irradiation or a chemical mutagen such as N-methyl-N'-nitrosoguanidine and the like, and then selecting the strains which have an increased ability to secreto-produce proteins.

Especially, *Corynebacterium glutamicum* AJ1203 (FERM BP-734) (originally deposited on Mar. 26, 1984) (currently, National Institute of Advanced Industrial Science and Technology, International Patent Organism Depositary, Tsukuba Central 6, 1-1, Higashi 1-Chome, Tsukuba-shi, Ibaraki-ken, 305-8566, Japan), was isolated from the wild-type *Corynebacterium glutamicum* (*C. glutamicum*) ATCC13869 as a streptomycin-resistant mutant strain. This strain is expected to have a mutation in a functional gene associated with protein secretion, and its ability to secreto-produce heterologous proteins is extremely high—approximately 2- or 3-fold as compared with the parent (wild-type) strain—under optimum culture conditions. Therefore, this strain is suitable as a host bacterium (see WO 02/081694). In addition, it is preferable to use a strain which was obtained by modifying a host strain such that the strain no longer produces the cell surface protein, because the purification of the heterologous proteins secreted in the medium will be easier, so it is particularly preferable. Such a modification can be performed by introducing a mutation into the cell surface protein gene on the chromosome or into its expression regulatory region through mutagenesis or gene recombination techniques.

Examples of promoters from a coryneform bacterium include promoters for the genes of the cell surface proteins PS1, PS2, and SlpA, promoters for the genes in biosynthetic systems of various amino acids, for example, glutamine synthetase gene, aspartokinase gene in the lysine biosynthetic system, and the like.

The signal peptide which is used in the present invention is the signal peptide for a secretory protein from coryneform bacterium, the host, and preferably it is the signal peptide of a cell surface protein from a coryneform bacterium. The cell surface proteins of coryneform bacteria include PS1 and PS2 from *C. glutamicum* (JP-Kokai No. 6-502548), and SlpA from *C. ammoniagenes* (JP-Kokai No. 10-108675).

To produce a neutral metalloprotease whose activity for selective cleavage of a pro-structure of a pro-MTG is strong by using recombinant DNA techniques, a DNA encoding such a neutral metalloprotease is required.

In one embodiment of the present invention, the neutral metalloprotease SVP35 is produced by using recombinant DNA techniques. The DNA encoding SVP35 can be obtained as follows.

First, the amino acid sequence of the purified SVP35 is determined. The Edman method (Edman, P., Acta Chem. Scand. 4, 227 (1950)) can be used to determine the amino acid sequence. The gas-phase protein sequencer from Shimadzu Co. Ltd. Co. Ltd. and the like can also be used to determine the amino acid sequence.

For the neutral metalloprotease SVC35 according to the present invention, the sequence shown in SEQ ID NO: 1 has been found by sequencing 20 amino acid residues from the N-terminus.

This information can be used to synthesize an appropriate primer for PCR and generate a probe to obtain the neutral metalloprotease according to the present invention. For example, a protease gene from actinomycetes, which is expected to have a homology based on the search results for the homology in the N-terminal amino acid sequence, for example, a metalloprotease (GenBank/EMBL/DDBJ CAB76001) gene from *Streptomyces coelicolor* can be subjected to PCR using an actinomycetes DNA prepared by the method of Saito and Miura [Biochem. Biophys. Acta, 72, 619 (1963)] as a template, to amplify the fragment of the gene encoding this protease. The amplified fragment can be used as a probe.

Then, the actinomycetes DNA prepared by the method of Saito and Miura, for example, the chromosomal DNA of *Streptoverticillium mobaraense* IFO13819, is digested with appropriate different restriction enzymes, for example various restriction enzymes which recognize 6-base sequences. The digested actinomycetes chromosomal DNA can be analyzed by techniques well known to those skilled in the art such as the Southern blot hybridization technique described in Molecular Cloning 2nd edition [J. Sambrook E. F. Fritsch and T. Maniatis, Cold Spring Harbor Laboratory Press, p 9. 31 (1989)] and the like by using the $^{32}$P-labeled PCR-product obtained by the above-described PCR. For example, the nucleic acid molecule encoding the neutral metalloprotease according to the present invention or the part thereof can be cloned by recovering the fragment which has been confirmed by Southern blot to have a high homology with the chosen probe, and cloning it into an appropriate vector. The techniques necessary for such a gene cloning are well known to those skilled in the art (see for example, J. Sambrook E. F. Fritsch and T. Maniatis, Cold Spring Harbor Laboratory Press, p 1. 90 (1989)).

In one embodiment of the present invention, PCR is performed using the chromosomal DNA of *Streptomyces coelicolor* A3(2) as a template to produce a probe. Furthermore, a single band of about 8 kb which is able to hybridize with $^{32}$P-labeled probes detected in the digested product of *Streptoverticillium mobaraense* IFO13819 chromosomal DNA digested with SphI. Thus, the chromosomal DNA of *Streptoverticillium mobaraense* IFO13819 prepared by the foregoing method is digested with SphI, the fragment of about 8 kb is recovered through an agarose gel electrophoresis, the recovered fragment is introduced at the SphI site in pUC18, and then it is introduced into a competent cell of *Escherichia coli* JM109 to generate a library. The clones of interest can be obtained by screening the generated library using a synthetic oligonucleotide as a probe according to colony hybridization techniques described in Molecular Cloning 2nd edition (supra), and selecting the strain which harbors the plasmid containing the gene fragment of SVP35 cloned into the plasmid. The plasmid recovered from this strain is herein designated pVSV1. The nucleotide sequence of the fragment cloned into pVSV1 is analyzed, the primary amino acid sequence is deduced to confirm that the fragment encodes the previously determined N-terminal amino acid sequence. Thus, the obtained gene is confirmed to be the gene encoding SVP35.

Then, a recombinant nucleic acid molecule can be constructed to express the neutral metalloprotease according to the present invention by ligating a genetic construct containing the DNA encoding the obtained metalloprotease to an appropriate vector depending on the properties of the chosen host. The host coryneform bacterium cells are transformed with the recombinant nucleic acid molecule. The transformed cells can be cultured in a suitable medium to recover the neutral metalloprotease according to the present invention which is secreted and/or accumulates in the medium and/or in the cell.

Next, a method of producing an active MTG from pro-MTG using the neutral metalloprotease will be described.

The neutral metalloprotease used in the production of an active MTG can be reacted with a pro-MTG as a fraction containing the neutral metalloprotease prepared from the culture medium of a neutral metalloprotease producing bacterium. It can be also used as a more highly purified neutral metalloprotease with high specific activity. Furthermore, as described below, the neutral metalloprotease can be also used, wherein the neutral metalloprotease can be obtained by culturing the cell transformed with a recombinant nucleic acid molecule which may be obtained by connecting a DNA encoding a neutral metalloprotease having strong selective cleavage activity for a pro-structure part of pro-MTG.

The pro-MTG used to produce MTG may be a fraction containing the pro-MTG prepared from the culture medium a pro-MTG producing bacterium. More highly purified pro-MTG may also be used. The reaction may be performed under conditions such that the amount of a neutral metalloprotease added to the pro-MTG is from $\frac{1}{10}$ to $\frac{1}{500}$ by weight and is appropriately adjusted within the reaction temperature of between 15° C. and 50° C. and the pH range of between pH 5.0 and 9.

In addition, the genetic construct, which is constructed as described above and which contains the DNA encoding the neutral metalloprotease according to the present invention, may be introduced into a microorganism containing the genetic construct encoding a pro-MTG, in particular, into a coryneform bacterium, to produce in a single bacterial cell both the pro-MTG and the neutral metalloprotease according to the present invention, thereby the pro-MTG may be converted into a mature MTG under the above conditions. A more detailed method for efficiently producing a pro-MTG in coryneform cells, the genetic construct used for such a method, and a coryneform bacterium into which the genetic construct has been introduced are disclosed in, for example WO 01/23591. More specifically, for example, a coryneform bacterium which can efficiently secrete a pro-MTG protein extracellularly may be obtained by introducing a genetic construct into a coryneform bacterium, wherein the genetic construct is obtained by connecting the sequence encoding a pro-MTG, which is located downstream of the sequence encoding the signal peptide domain of a coryneform bacterium, particularly the signal peptide domain of a cell surface protein, downstream of an appropriate promoter. The signal peptide, promoter, and host which can be used for this purpose can be selected from signal peptides, promoters, and hosts which are suitable for expressing the neutral metalloproteases according to the present invention and as mentioned above. A combination of vectors that are compatible in the same cell is also well known to those skilled in the art. Therefore, the mature MTG can be obtained by introducing an appropriate genetic expression construct containing the DNA encoding the neutral metalloprotease according to the present invention as mentioned above into a coryneform bacterium producing a pro-MTG, or vice versa, by introducing an appropriate genetic expression construct encoding a pro-MTG into coryneform bacterium producing the neutral metalloprotease according to the present invention, thereby allowing the genetic constructs which can express the pro-MTG and the neutral metalloprotease according to the present invention to coexist in the same bacterium, culturing the bacterium, and maintaining the culture under appropriate conditions such that the neutral metalloprotease according to the present invention is active.

The transglutaminase produced by the method according to the present method can be isolated and purified from the reaction mixture according to methods well known to those skilled in the art. For example, the transglutaminase can be isolated and purified by removing the cells from the mixture by centrifugation, etc. and then by using known appropriate methods such as salting-out, ethanol precipitation, ultrafiltration, gel filtration chromatography, ion-exchange column chromatography, affinity chromatography, medium high-pressure liquid chromatography, reversed-phase chromatography, hydrophobic chromatography, or a combination thereof.

The present invention is further described in the following non-limiting Examples.

EXAMPLES

Example 1

Neutral Metalloprotease Produced by *Streptoverticillium mobaraense* IFO13819

(1) Purification of Neutral Metalloprotease (SVP70) Produced by *Streptoverticillium mobaraense* IFO13819

800 mL of ISP2 culture medium (4 g of Yeast Extract, 10 g of Malt Extract, 4 g of Glucose per liter of water, adjusted to pH 7.3) was placed in a 5 L Sakaguchi flask (shaking flask), and was inoculated with *Streptoverticillium mobaraense* IFO13819 from a plate, and cultured by shaking at 30° C. for 9 days at 120 rpm. The culture medium was centrifuged, and the supernatant of the culture was collected. It was filtered using a Depth filter (3 µm of pore size, Sartorius Co. Ltd.), followed by concentration using Sartocon Slice membrane having a pore size of 10,000 Da (Saltorius Co. Ltd.). The concentrate was diluted 10-fold with Tris-HCl buffer/5 mM calcium chloride (pH 7.5), subjected to a DEAE-Sepharose FF (2.6 φ×10 cm, Amersham Pharmacia Co. Ltd.) column equilibrated with the same buffer, using FPLC (Amersham Pharmacia Co. Ltd.), and eluted using a linear concentration gradient of 0-0.5 M sodium chloride. A fraction containing the active ingredient was collected, subjected to a phenyl Sepharose HP (1.6 φ×10 cm, Amersham Pharmacia Co. Ltd.) column equilibrated with 1.5 M ammonium sulfate/20 mM MES buffer/5 mM calcium chloride (pH 6.0), eluted using linear concentration gradient of 1.5-0 M ammonium sulfate, and an active fraction was collected. The resulting active fraction was dialyzed against 20 mM MES buffer/5 mM calcium chloride (pH 6.0) at 4° C. overnight to obtain a purified enzyme solution.

The measurement of the enzyme activity at each step was carried as follows:

The enzyme solution was added to 20 mM sodium phosphate buffer containing peptide GPSFRAPDS (Peptide Institute) (SEQ ID NO: 11) to yield 170 µl of total liquid volume, and it was reacted at 30° C. for 10 minutes, followed by heating at 95° C. for 5 minutes to terminate the reaction. 80 µl of this solution was analyzed by HPLC under the following conditions and its activity was calculated based on the decreased amount of the substrate.

Apparatus: HPLC L-6300 system (Hitachi Co. Ltd).
Column: YMC-PACK ODS 120 A 4.6×150 mm (YMC)
Eluent: (A) 0.1% TFA (B) 80% acetonitrile/0.1% TFA
Eluting condition: linear concentration gradient of 12-16% acetonitrile (for 15 minutes)
Flow rate: 1.0 ml/min
Detection wavelength: 220 nm Under these conditions, the peptide GPSFRAPDS (SEQ ID NO. 11) was eluted for 13 to 14 minutes of retention time, and the degraded product FRAPDS (SEQ ID NO. 12) was eluted for 7.5 to 8.5 minutes of retention time.

The amount of the enzyme that catalyzes one (1) nmol of pro-MTG degradation in a minute was defined as one (1) unit of the enzyme activity.

(2) Purification of Neutral Metalloprotease (SVP35) Produced by *Streptoverticillium mobaraense* IFO13819

800 mL of ISP2 culture medium was placed in a 5 L of Sakaguchi flask and was inoculated with *Streptoverticillium mobaraense* IFO13819 from a plate, and cultured by shaking at 30° C. for 48 hours at 120 rpm. The culture medium was centrifuged, and the supernatant of the culture was discarded to harvest cells. The cells were suspended in 20 mM Tris-HCl buffer/30 mM sodium chloride (pH 7.5), shaken on ice for 4 hours, and then the supernatant was collected by centrifugation. The supernatant obtained was filtered and sterilized using a Depth filter (0.22 µm of pore size, made by Sartorius Co. Ltd.), and then it was subjected to a CM-Sepharose FF (Amersham Pharmacia Co. Ltd.) column (1.6 φ×10 cm) equilibrated with 20 mM Tris-HCl buffer (pH 7.5) containing 5 mM calcium chloride and 0.01 mM zinc chloride, using FPLC (Amersham Pharmacia Co. Ltd.), eluted in the same buffer using a linear concentration gradient of 0-0.5 M sodium chloride. A fraction containing the active ingredient was collected, and was further subjected to Phenyl-Sepharose HP column (1 mL, Amersham Pharmacia Co. Ltd.) equilibrated with 20 mM Tris-HCl buffer containing 1.5 M ammonium sulfate, 5 mM calcium chloride and 0.01 mM zinc chloride, and eluted using a linear concentration gradient of 1.5-0 M ammonium sulfate. An active fraction was collected, and demineralized by 20 mM Tris-HCl buffer (pH 7.5) containing 5 mM calcium chloride and 0.01 mM zinc chloride, using PD-10 column (Amersham Pharmacia) to give a partially purified enzyme solution.

The enzyme activity at each step was measured using the peptide GPSFRAPDS as a substrate in the same manner as in (1).

(3) Evaluation of the Properties of the Neutral Metalloprotease (SVP35) Produced by *Streptoverticillium mobaraense* IFO13819 i) Substrate Specificity 1 mg/ml of insulin B solution and pro-MTG solution prepared in 20 mM Tris-HCl buffer (pH 7.5) containing 5 mM calcium chloride and 0.01 mM zinc chloride was used as a substrate, and an enzyme solution was added to the solution to react at 30° C. for 2 hours, and then peptide fragments were separated by HPLC under the following conditions:

Apparatus: L-7100/7200/7405/D-7600 (Hitachi Co. Ltd.)
Column: VYDAC C18 4.6 mm I.D.×250 mm (VYDAC)
Eluent: (A) 0.1% TFA (B) 80% acetonitrile/0.1% TFA
Eluting condition: linear concentration gradient of 4-44% acetonitrile
Flow rate: 0.5 ml/min
Detection wavelength: UV 220 nm The amino acid sequences of the obtained peptide fragments were analyzed by PPSQ-10 (Shimadzu Co. Ltd.) to characterize the sequences of the cleavage points for SVP35. As a result, it was confirmed that the peptide was cleaved before (at the N-terminal of) especially Phe, often Leu, sometimes Tyr, Trp, Ile, Val, and that SVP recognized the aromatic amino acids and hydrophobic amino acids with bulky side-chains positioned at P' 1 of the cleavage site.

ii) Optimum pH

In 0.15 M GTA buffer (buffered by 3,3-dimethyl glutaric acid, Tris (hydroxy methyl) amino methane, 2-amino-2-methyl-1,3-propanediol) from pH 3 to pH 10, SVP35 was allowed to act on Gly-Pro-Ser-Phe-Arg-Ala-Pro-Asp-Ser (SEQ ID NO: 11) as a substrate at 30° C. for 10 minutes. As a result, it was revealed that the Optimum pH of SVP35 was around 7.0, and that when the activity at pH 7.0 was defined as 100%, SVP35 had an activity of 70% or more at pH 6.0-8.0 and an activity of 80% or more at pH 6.5-7.5 (see FIG. 1).

iii) pH Stability

Figure 2:
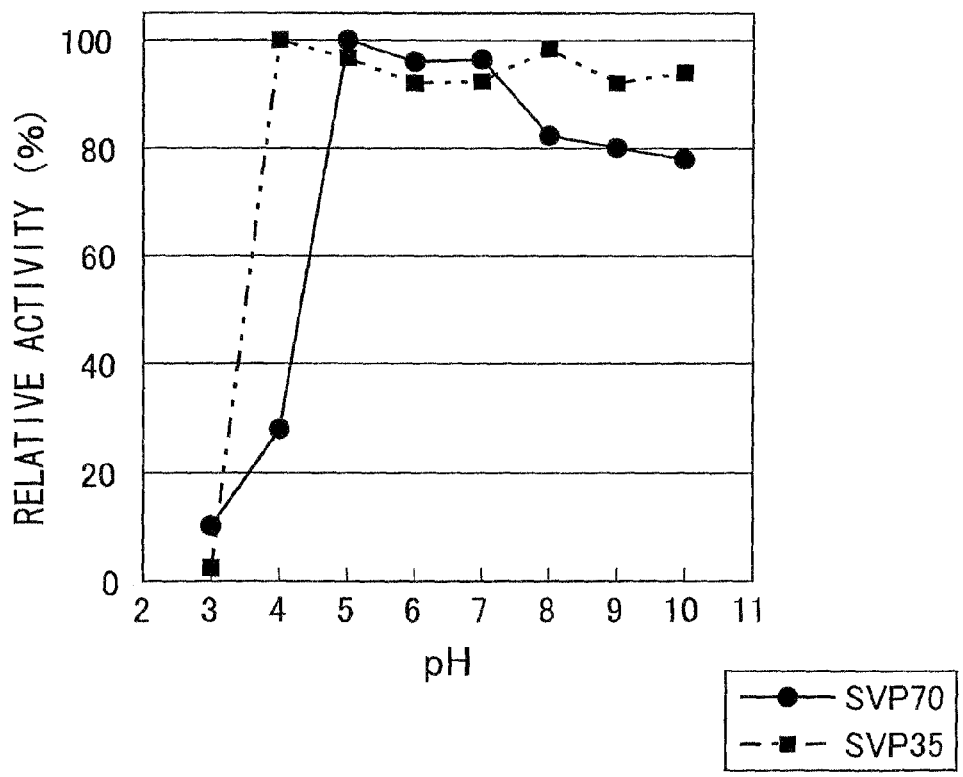
FIG. 2 is a graph which shows the pH stability of SVP35 and SVP70.

To 10 µl of SVP35 purified enzyme solution, 40 µl of each pH of 0.15 M GTA buffer from pH 3 to pH 10 was added, left at 4° C. overnight, followed by addition of 0.1 M sodium phosphate buffer (pH 7.0) to the liquid volume of 400 µl, and was adjusted to pH 7.0. To these enzyme solutions, Gly-Pro-Ser-Phe-Arg-Ala-Pro-Asp-Ser (SEQ ID NO: 11) was added as a substrate, and reacted at pH 7.0, at 30° C. for 10 minutes. As a result, it was shown that SVP35 was stable within the range of pH 4 to pH 10 (when the activity at pH 4.0 was defined as 100%, it had an activity of 90% or more at pH 4-10) (see FIG. 2).

iv) Optimum Temperature

Figure 3:
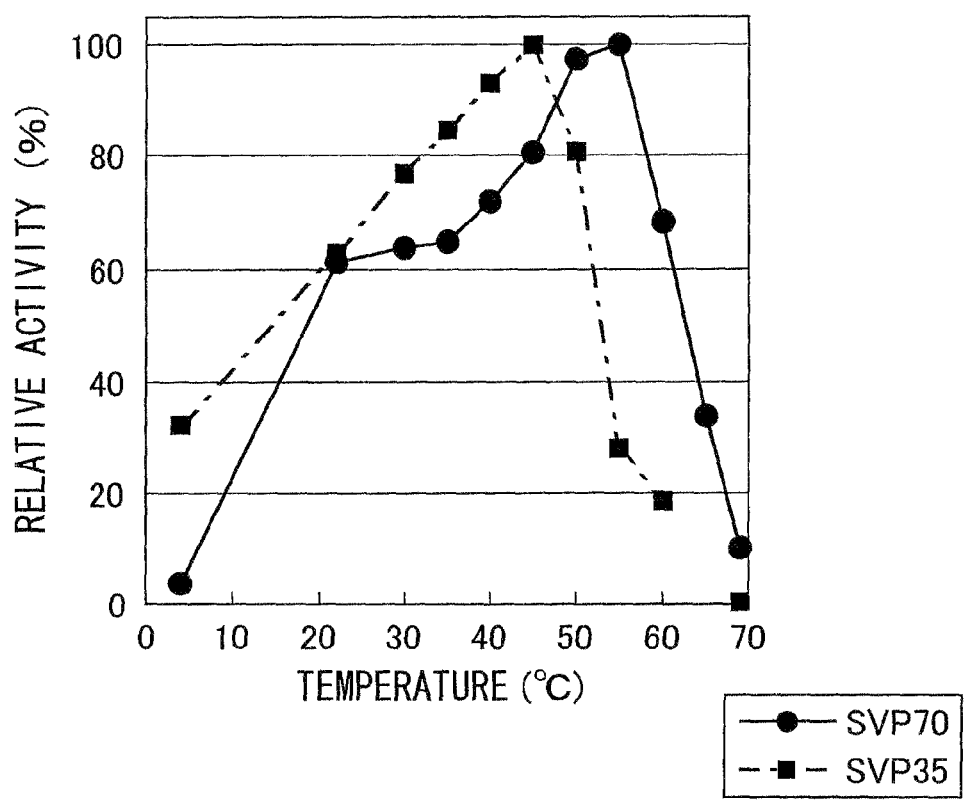
FIG. 3 is a graph which shows the temperature dependence of SVP35 and SVP70 activity.

To the purified enzyme solution diluted with 20 mM Tris-HCl buffer (pH 7.5) containing 5 mM calcium chloride and 0.01 mM zinc chloride Gly-Pro-Ser-Phe-Arg-Ala-Pro-Asp-Ser (SEQ ID NO: 11) was added and reacted at pH 7.0, between 5° C. and 65° C. for 10 minutes. As a result, it was shown that the Optimum temperature of SVP35 was about 45° C. and it had high activity within the range of 40° C. to 50° C. (it had an activity of 80% or more than that at 45° C.) (see FIG. 3).

v) Temperature Stability

Figure 4:
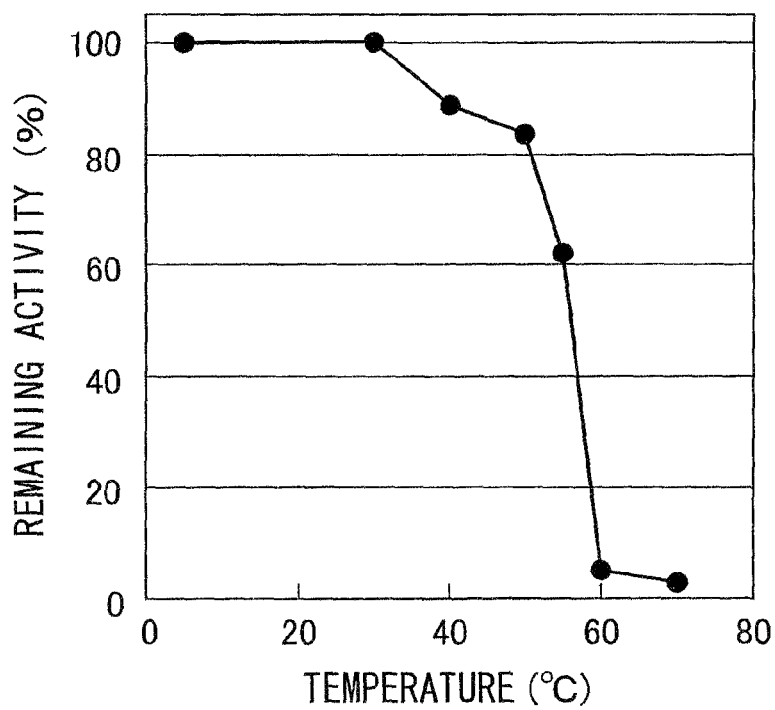
FIG. 4 is a graph which shows the temperature stability of SVP35.

To 10 µl of the purified enzyme solution, 40 µl of 20 mM Tris-HCl buffer (pH 7.5) containing 5 mM calcium chloride and 0.01 mM zinc chloride was added to treat at 4° C. or at from 30° C. to 70° C. for 15 minutes, and then cooled by ice, added 250 µl of 20 mM sodium phosphate buffer (pH 7.0). To this enzyme solution, Gly-Pro-Ser-Phe-Arg-Ala-Pro-Asp-Ser (SEQ ID NO: 11) was added as a substrate and reacted at 30° C. for 5 minutes. When the activity treated at 4° C. was defined as 100%, the remaining activity at each temperature was calculated. As a result, it was shown that SVP35 retained 80% of activity at 50° C., but it lost its activity at 60° C. (see FIG. 4).

vi) Inhibitors

Figure 5:
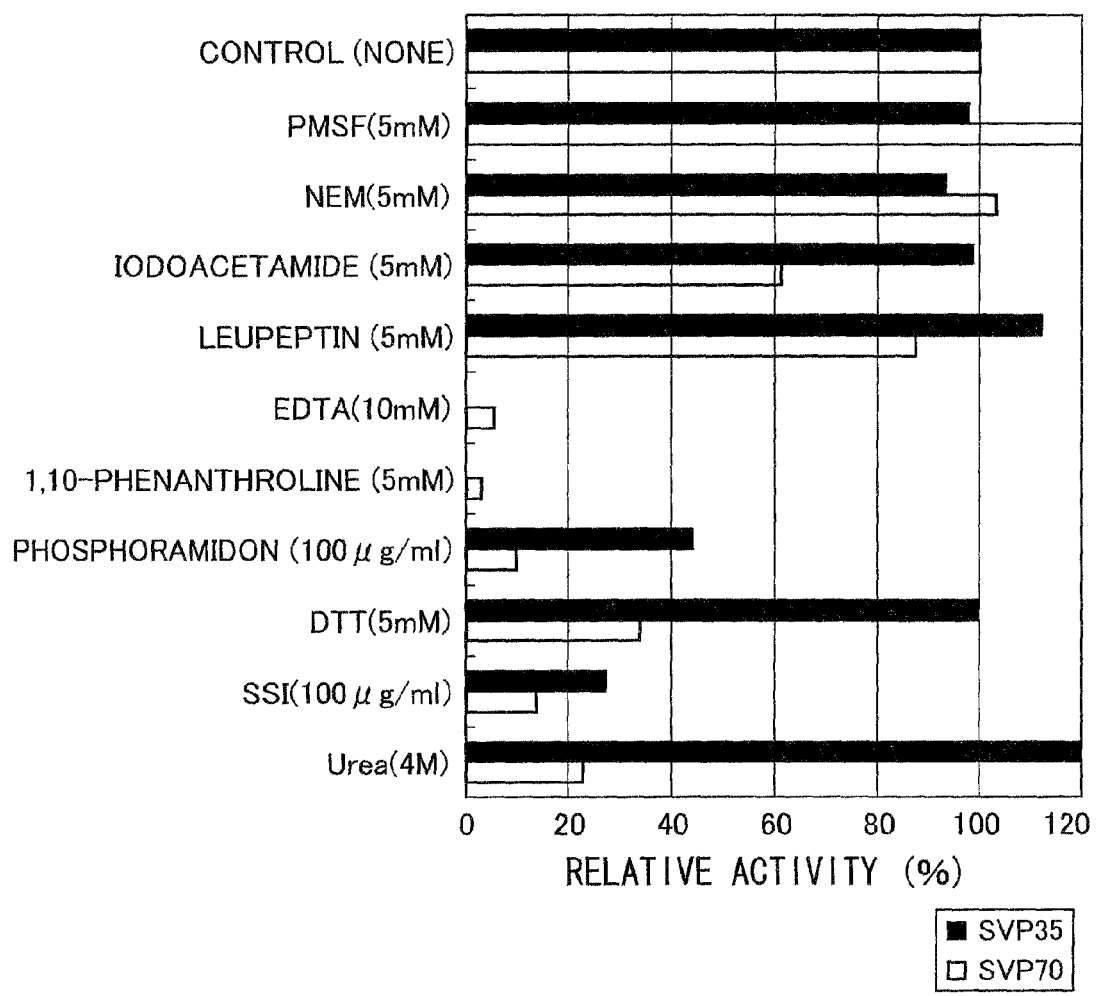
FIG. 5 depicts the inhibitory activities of various compounds to SVP35 and SVP70 activity.

To 20 mM sodium phosphate buffer (pH 7.0) containing various compounds at the concentrations shown in FIG. 5, the purified enzyme solution was added and left for 60 minutes at room temperature. Then Gly-Pro-Ser-Phe-Arg-Ala-Pro-Asp-Ser (SEQ ID NO: 11) was added as a substrate and reacted for 10 minute at 30° C. The relative activity by adding each compound was calculated based on the Gly-Pro-Ser-Phe-Arg-Ala-Pro-Asp-Ser (SEQ ID NO: 11) cleavage activity in the absence of compounds as 100%. As a result, it was shown that SVP35 was strongly inhibited by ethylene diamine tetraacetic acid, 1,10-phenanthroline and phosphoramidon which are metalloprotease inhibitors, and by *Streptomyces* subtilisin inhibitor (SSI) derived from actinomycetes (see FIG. 5).

(4) Characterization of the Properties of the Neutral Metalloprotease (SVP70) Produced by *Streptoverticillium mobaraense* IFO13819 i) Substrate Specificity

The substrate specificity was examined similarly as described in (3)-i). As a result, it was revealed that the substrate was cleaved before (at N-terminal side of) especially Phe, often Leu, sometimes Tyr, Trp, Ile, Val, and that SVP70 recognized the aromatic amino acids and hydrophobic amino acids with bulky side-chains positioned at P' 1 of the cleavage site.

ii) Optimum pH

The Optimum pH of SVP70 was examined similarly as (3)-ii). As a result, it was revealed that the Optimum pH of SVP70 was around 7.0, and that if the activity at pH 7.0 is defined as 100%, SVP70 had an activity of 90% or more at pH 6.0-8.0 and an activity of 95% or more at pH 6.5-7.5 (see FIG. 1).

iii) pH Stability

The pH stability was examined similarly to (3)-iii). As a result, it was shown that SVP70 was stable within pH 5 to pH 10, but it was less stable than SVP35 at slightly alkaline (see FIG. 2). Specifically, if the activity at pH 5.0 was defined as 100%, it had an activity 90% or more in the range of pH 5 to pH 7, and it had an activity about 80% or more even in the range of pH 7 to pH 10.

iv) Optimum Temperature

The Optimum temperature of SVP70 was examined similarly as (3)-iv). As a result, it was shown that the Optimum temperature of SVP70 was within the range from about 50° C. to 55° C., especially around 55° C. (see FIG. 3).

v) Inhibitors

The inhibitory activities of various compounds to SVP70 were examined analogously to (3)-vi). As a result, SVP70 underwent strong inhibitory action by ethylene diamine tetraacetic acid, 1,10-phenanthroline, and phosphoramidon, which are metalloprotease inhibitors, and by reductant dithiothreitol, urea, and *Streptomyces* subtilisin inhibitor (SSI) derived from actinomycetes (see FIG. 5).

(5) Sequencing of the N-Terminal Amino Acid Sequence of SVP35 and SVP70

The purified enzymes of SVP35 and SVP70 obtained in (1) and (2) above were transferred onto Polyvinilidene-difluoride (PVDF) membrane using Membrane Cartridge (Perkin Elmer Co. Ltd.) and the N-terminal amino acid sequence was analyzed using a gas-phase Protein Sequencer PPSQ-10 (Shimadzu Co. Ltd.). The amino acid sequence of SVP35 is shown in SEQ ID NO: 1, and the amino acid sequence of SVP70 is shown in SEQ ID NO: 2. A homology can be seen in these sequences.

Accordingly, those which had any homology to these proteases for N-terminal amino acid sequences were searched, and then metalloprotease SGMP II (J. Biochem., Vol. 110, p. 339-344, 1991) from *Streptomyces griseus*, and three metalloproteases (GenBank/EMBL/DDBJ CAB76000, the same CAB76001, and the same CAB69762), etc. from *Streptomyces coelicolor* were found. These proteases also can be used to cleave selectively the pro-structure part of the pro-MTG, and therefore they can be used to produce an active MTG according to the present invention.

(6) Cloning of SVP35 Gene and its Secretory Expression in Coryneform Bacteria

The chromosomal DNA of *Streptomyces coelicolor* A3(2) was prepared using the method of Saito and Miura [Biochem. Biohhys. Acta, 72, 619 (1963)]. Primers shown in SEQ ID NO: 3 and SEQ ID NO: 4 were synthesized by referring to the sequence of metalloprotease (GenBank/EMBL/DDBJ CAB76001) gene from *Streptomyces coelicolor* which have a homology in the N-terminal amino acid sequence. Primers shown in SEQ ID NO: 3 and SEQ ID NO: 4 were used to perform PCR using the chromosomal DNA of *Streptomyces coelicolor* A3(2) as a template, and the gene region in the metalloprotease gene was amplified. For the PCR reaction, Pyrobest DNA polymerase (Takarasyuzo Co. LTD.) was used and the reaction conditions followed the protocol recommended by the manufacturer. The chromosomal DNA of *Streptoverticillium mobaraense* IFO13819 prepared by the method of Saito and Miura was digested by various restriction enzymes which recognize 6-base sequence, the digested samples were analyzed by the Southern blot hybridization as described in Molecular Cloning 2nd edition [J. Sambrook E. F. Fritsch and T. Maniatis, Cold Spring Harbor Laboratory Press, p 9. 31 (1989)], using the $^{32}$P-labeled PCR product as a probe, and a single band of about 8 kb was detected by SphI cleavage. Accordingly, the chromosomal DNA of *Streptoverticillium mobaraense* IFO13819 which had been prepared by the foregoing method was digested with SphI, and a fragment of about 8 kb was recovered through agarose gel electrophoresis using EASYTRAP Ver. 2 (Takarasyuzo Co. LTD.). The recovered fragment was inserted into SphI site of pUC18, which was introduced into competent cells of *Escherichia coli* JM109 (Takarasyuzo Co. LTD.) to generate a library. The library was screened for the bacterial strain which contains the plasmid where the SVP35 gene fragment was cloned, by colony hybridization as described in Molecular Cloning 2nd edition [J. Sambrook E. F. Fritsch and T. Maniatis, Cold Spring Harbor Laboratory Press, p 1. 90 (1989)], using the synthetic nucleotide as a probe.

The plasmid was recovered from the strain obtained above and was designated as pVSV1. The nucleotide sequence of the fragment cloned in pVSV1 was determined. The nucleotide sequence of this cloned fragment is shown in SEQ ID NO: 5. The primary amino acid sequence encoded by this gene was deduced, which allowed the determination of the entire primary amino acid sequence of SVP35 containing the signal sequence of SVP35 including the amino acid sequence of the previously determined N-terminal portion and the region assumed to be a pro-structure part. The entire amino acid sequence of SVP35 is shown in SEQ ID NO: 6. It is presumed that amino acid nos. 1-36 of amino acid sequence described in SEQ ID NO: 6 refer to the signal sequence, amino acids nos. 37-216 refer to the pro-structure part, and amino acids nos. 217-537 correspond to the mature SVP35.

Primers shown in SEQ ID NO: 7 and SEQ ID NO: 8 were synthesized using pVSV1 as a template by referring to the sequence of SEQ ID NO: 5, and the gene region containing the pro-structure part of SVP35 and the mature SVP35 was amplified by PCR. For the PCR reaction, Pyrobest DNA polymerase (Takarasyuzo Co. Ltd.) was used and the reaction conditions followed the protocol recommended by the manufacturer.

Next, using pPKSPTG1 described in WO 01/23591 as a template, the region including the 5'-upstream region containing the promoter region of PS2 gene which is the cell surface protein of *C. glutamicum* and the signal sequence of SlpA, the cell surface protein of *C. ammoniagenes* was amplified by PCR technique using the combination of oligonucleotides of SEQ ID NO: 9 and SEQ ID NO: 10. The primer shown in SEQ ID NO: 10 contains the sequence encoding the N-terminal amino acids of SVP35 having a pro-structure part.

Then, the gene of the heterologous fusion pre-pro SVP35 gene fragment, which was connected to the 5'-upstream region comprising the promoter region of PS2 gene and the signal sequence of SlpA, the cell surface protein, from *C. ammoniagenes*, was amplified by performing cross-over PCR with SEQ ID NO: 8 and SEQ ID NO: 9 using the mixture of 1 µl each of the amplified PCR solution. The amplified fragment of about 2.3 kb was detected by agarose gel electrophoresis. The PCR product was subjected to agarose gel electrophoresis to recover a fragment of about 2.3 kb, and after blunting its ends using DNA Blunting Kit (Takarasyuzo Co. Ltd.), the fragment was inserted into SmaI site of pCV7 as described in JP-Kokai No. 9-070291 to obtain pVSV1. The nucleotide sequence of the inserted fragment was determined according to a conventional method to confirm that the fusion gene was constructed as expected.

*C. glutamicum* ATCC13869 was transformed with the constructed pVSV1 and the strains which grew on the CM2S agar medium containing 5 mg/l of chloramphenicol (10 g of yeast extract, 10 g of tryptone, 5 g of sucrose, 5 g of NaCl, 15 g of agar per liter of distilled water) were selected. Then, the selected *C. glutamicum* ATCC13869 harboring pVSV1 was cultured in MMTG culture medium (60 g of glucose, 0.4 g of magnesium sulfate heptahydrate, 30 g of ammonium sulfate, 1 g of potassium dihydrogenphosphate, 0.01 g of ferrous sulfate heptahydrate, 0.01 g of manganese sulfate pentahydrate, 450 µg of thiamine hydrochloride, 450 µg of biotin, 0.15 g of DL-methionine, 50 g of calcium carbonate per liter of distilled water, adjusted to pH 7.5) containing 5 mg/l of chloramphenicol at 30° C. for 30 hours. 1 ml of the culture medium was centrifuged to separate to the supernatant of the culture and the bacteria. The activity of SVP35 was detected in the supernatant of the culture, and as a result of SDS-PAGE (Nature, 227, 380-685 (1970)) electrophoresis according to Laemmli's method, it was confirmed that about 200 mg/L of SVP35 was secretory-expressed.

Example 2

Figure 6:
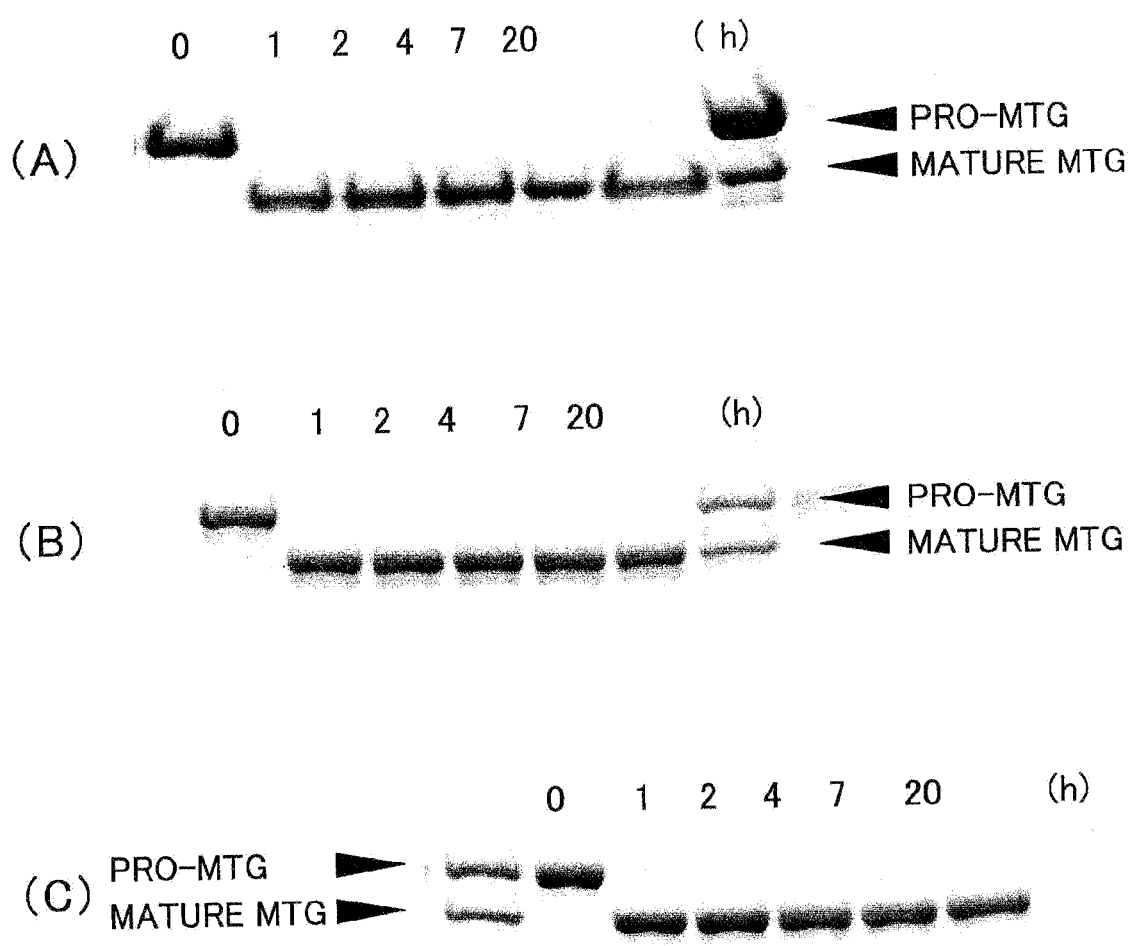
FIGS. 6 (A), (B), and (C) depict the sequential change of the conversion of pro-MTG to an active MTG by SVP35 (A) and SVP70 (B) from *Streptoverticillium mobaraense*, and by neutral metalloprotease SGMPII (C) from *Streptomyces griseus*, relative to the change in the protein amount. The lanes represents the time elapsed, as indicated by the "(h)" notation in the figure panels.

Conversion of Transglutaminase from *Streptoverticillium mobaraense* IFO13819 (Pro-MTG) into an Active Form Using pro-MTG (1 mg/ml) expressed by *Corynebacterium glutamicum* as a purified substrate, the neutral protease (SVP35, SVP70) from *Streptoverticillium mobaraense* or the neutral metalloprotease SGMP II from *Streptomyces griseus* was mixed in the ratio of the substrate:the enzyme=200:1, the mixture was reacted at 30° C. After 0, 1, 2, 4, 7, 20 hours, the reaction mixture was sequentially picked up, and the aliquots of the reaction mixture were mixed with SDS-PAGE sample buffer and heated at 95° C. for 3 minutes, and then subjected to SDS-PAGE according to Laemmli's method (Nature, 227, 680-685 (1970)). The result is shown in FIG. 6. As can be seen in FIG. 6, when these proteases were reacted, pro-MTGs were converted to the mature forms, and the produced MTGs were not reduced even after a long-term reaction. The transglutaminase (TG) activity of the picked up fraction was measured by the hydroxamate method, and sufficient activity was confirmed. In addition, SGMP II was purified from actinase (Kakenseiyaku Co. Ltd.) according to the reference method (J. Biocem., Vol. 110, p. 339-344, 1991).

Figure 7:
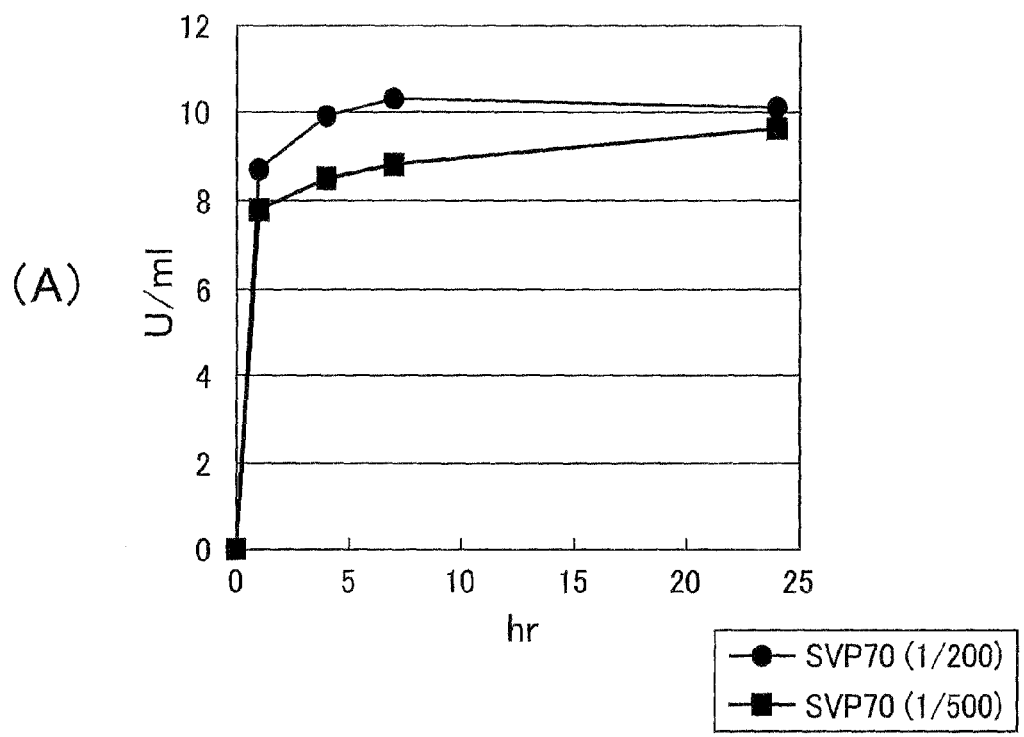
FIGS. 7 (A) and (B) are graphs which depict the time course of transglutaminase activity, if a pro-MTG is reacted with SVP70 and SAM-P45, respectively. (A): SVP70 addition, ●: additional amount of 1/200 relative to substrate, ■: additional amount of 1/500 relative to substrate; (B): SAM-P45 addition, ♦: additional amount of 1/10 relative to substrate, ▲: additional amount of 1/50 relative to substrate.
Figure 7:
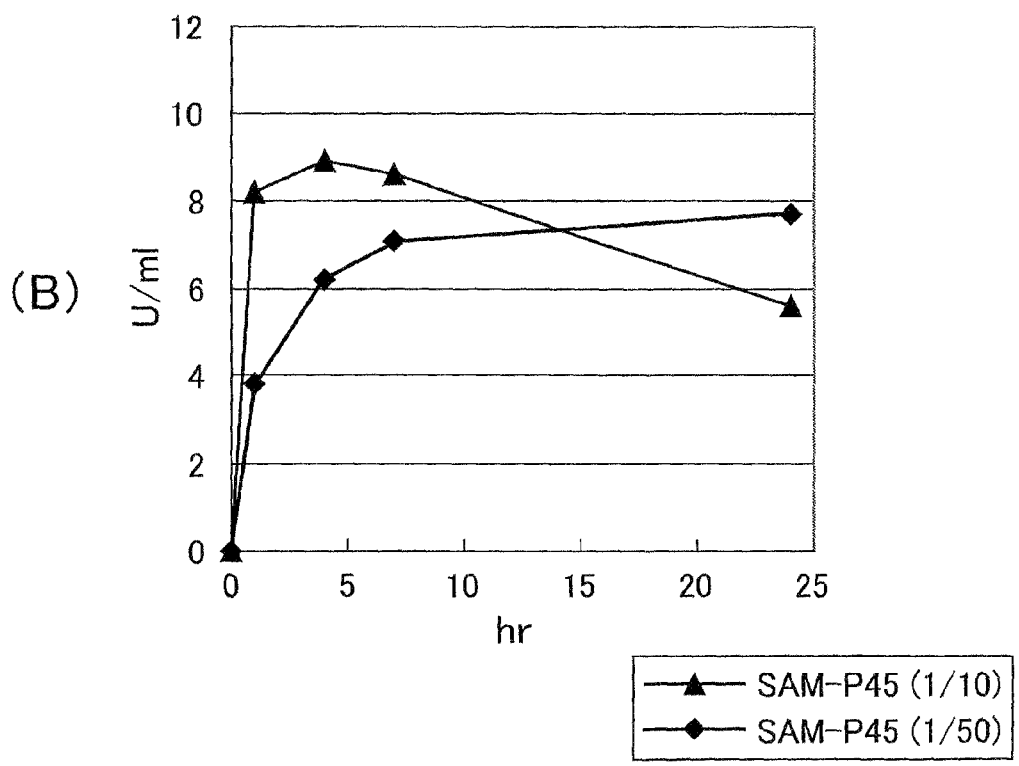
Figure 8:
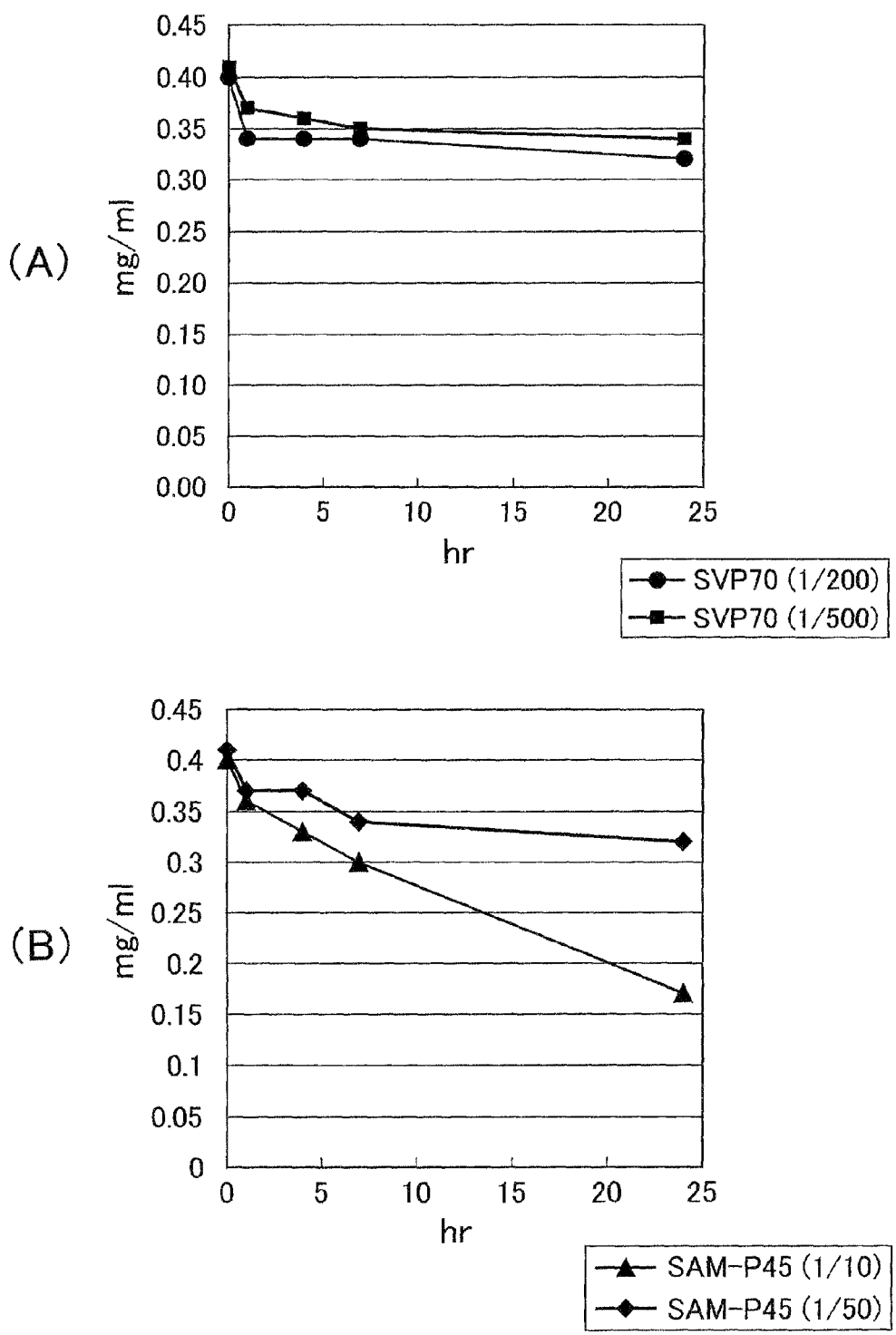
FIG. 8 (A) and (B) are graphs which depict the time course of the amount of pro-MTG protein, if a pro-MTG reacts with SVP70 and SAM-P45, respectively. (A): SVP70 addition, ●: additional amount of 1/200 relative to substrate, ■: additional amount of 1/500 relative to substrate; (B): SAM-P45 addition, ♦: additional amount of 1/10 relative to substrate, ▲: additional amount of 1/50 relative to substrate.

Then, the neutral metalloprotease SVP70 from Streptoverticillium mobaraense, and serine protease SAM-P45 (*Streptomyces albogriseolus*) as a control, were added to the pro-MTGs with gradually increasing amounts of these enzymes, and reacted at 30° C. and pH 7.0. After 1, 4, 7, and 24 hours, the reaction mixture was picked up sequentially to determine the TG activity by the hydroxamate method (see FIG. 7). The protein concentration of TG was measured by reverse phase chromatography (see FIG. 8). As a result, it was shown that SVP could convert pro-MTG to active MTG with an amount as small as 1/500 of the substrate. It was shown that SAM-P45 generated only insufficient transglutaminase activity even at an amount of 1/50 of the substrate, and that the complete conversion to the active form was not observed. On the other hand, when SAM-P45 was added at an amount of 1/10 of the substrate, the conversion into the active MTG was observed, but a decrease in the amount and the activity of MTG-protein was observed. This suggests that over-degradation of the mature MTG occurred by SAM-P45.

The present invention provides a new protease from an actinomycetes, *Streptoverticillium mobaraense*, which specifically cleaves the pro-structure part of transglutaminase precursor to activate it, and the gene thereof. The new protease according to the present invention can be expressed in a large amount by a coryneform bacterium, and thereby the present invention provides a method for efficiently producing transglutaminase from microorganisms.

The advantage of using the neutral metalloproteases from actinomycetes according to the present invention for the production of an active MTG is that these enzymes have strong activities for selectively cleaving the pro-structure part of the pro-MTG, and that these enzymes can be expressed extracellularly by a coryneform bacterium.

As it is shown that the pro-MTG from actinomycetes can be efficiently expressed and secreted by a coryneform bacterium, it is possible to produce more efficiently an active MTG by a single bacterial cell by co-expressing and secreting the pro-MTG and the neutral metalloprotease. In this instance, it is sufficient to express the neutral metalloprotease in only an amount required and sufficient for cleaving the pro-structure part of the pro-MTG.

While the invention has been described in detail with reference to preferred embodiments thereof, it will be apparent to one skilled in the art that various changes can be made, and equivalents employed, without departing from the scope of the invention. Each of the aforementioned documents, including the foreign priority document, JP 2003-061623, is incorporated by reference herein in its entirety.

REFERENCES

1. JP-Kokoku No. 1-50382
2. JP-Kokai No. 64-27471
3. WO publication No. 01/2351
4. JP-Kokai No. 6-502548
5. JP-Kokai No. 10-108675
6. Eur. J. Biochem., Vol. 257, pages 570-576, 1998,
7. J. Biochem., Vol. 110, pages 339-344, 1991.

What is claimed:

1. A biochemical method of producing an active *Streptoverticillium* transglutaminase from a *Streptoverticillium* protransglutaminase comprising:
   A) contacting a neutral *Streptoverticillium mobaraense* IFO 13819 metalloprotease with the protransglutaminase, and
   B) recovering the active *Streptoverticillium* microbial transglutaminase;
   wherein said metalloprotease comprises:
   a molecular weight of about 71,000,
   an optimum pH of 7.0,
   an optimum temperature of about 55° C.,
   an activity to cleave the peptide of SEQ ID NO: 11; and
   wherein said metalloprotease is strongly inhibited by ethylene diamine tetraacetic acid, 1,10-phenanthroline, phosphoramidon, dithiothreitol, and *Streptomyces* subtilisin inhibitor (SSI) from actinomycetes.

2. The method according to claim 1, wherein said microorganism is a coryneform bacterium.

3. The method according to claim 1, wherein the metalloprotease comprises, as an N-terminal amino acid sequence, the sequence of SEQ ID NO: 2.

* * * * *